United States Patent
Wiley et al.

(10) Patent No.: US 11,633,566 B2
(45) Date of Patent: Apr. 25, 2023

(54) CURVED CATHETER AND METHODS FOR MAKING SAME

(71) Applicant: C. R. Bard, Inc., Murray Hill, NJ (US)

(72) Inventors: Martha R. Wiley, Salt Lake City, UT (US); William R. Barron, Riverton, UT (US); Jordan P. Diamond, Salt Lake City, UT (US); Scott W. Snyder, West Valley City, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1069 days.

(21) Appl. No.: 16/362,550

(22) Filed: Mar. 22, 2019

(65) Prior Publication Data
US 2019/0217054 A1    Jul. 18, 2019

Related U.S. Application Data

(62) Division of application No. 14/152,599, filed on Jan. 10, 2014, now Pat. No. 10,252,023.
(Continued)

(51) Int. Cl.
*A61M 25/00* (2006.01)
*A61M 5/14* (2006.01)
(Continued)

(52) U.S. Cl.
CPC ...... *A61M 25/0009* (2013.01); *A61M 5/1418* (2013.01); *A61M 25/0013* (2013.01);
(Continued)

(58) Field of Classification Search
CPC .......... A61M 5/1418; A61M 2025/024; A61M 25/0009
See application file for complete search history.

(56) References Cited

U.S. PATENT DOCUMENTS

| 256,590 A | 4/1882 | Pfarre |
| 2,175,726 A | 10/1939 | Gebauer |

(Continued)

FOREIGN PATENT DOCUMENTS

| CA | 1092927 A | 1/1981 |
| CA | 1150122 A | 7/1983 |

(Continued)

OTHER PUBLICATIONS

McIntosh, Berry, Thompson, and Durham; Double Lumen Catheter for Use with Artificial Kidney; J.A.M.A.; Feb. 21, 1959; 137/835-138/836.

(Continued)

*Primary Examiner* — Deanna K Hall
(74) *Attorney, Agent, or Firm* — Rutan & Tucker LLP

(57) ABSTRACT

A pre-curved catheter tube of a catheter assembly or other elongate medical device and methods for forming such a device using a heating procedure is disclosed. Pre-curving of the catheter tube is desirable to impart to the catheter assembly a desired positional configuration when the catheter assembly is inserted into a patient. The heating procedure may include heat sterilization procedures commonly used to sterilize medical devices prior to use. One method for curving a catheter tube of a catheter assembly includes constraining the catheter tube into a curved configuration using the tube constraint, heating the catheter tube in the curved configuration for a predetermined time at a predetermined temperature, and releasing the catheter tube from the tube constraint after the heating is complete.

13 Claims, 10 Drawing Sheets

Related U.S. Application Data

(60) Provisional application No. 61/751,682, filed on Jan. 11, 2013.

(51) Int. Cl.
*B29C 53/08* (2006.01)
*A61M 25/02* (2006.01)

(52) U.S. Cl.
CPC .... *A61M 25/0021* (2013.01); *A61M 25/0041* (2013.01); *B29C 53/083* (2013.01); *A61M 2025/024* (2013.01); *Y10T 29/49* (2015.01)

(56) References Cited

U.S. PATENT DOCUMENTS

| | | | |
|---|---|---|---|
| 2,590,895 A | 4/1952 | Scarpellino | |
| 2,910,981 A | 11/1959 | Wilson et al. | |
| 3,055,361 A | 9/1962 | Ballard | |
| 3,096,551 A | 7/1963 | Shoberg | |
| 3,256,885 A | 6/1966 | Higgins et al. | |
| 3,434,691 A | 3/1969 | Hamilton | |
| 3,612,038 A | 10/1971 | Halligan | |
| 3,634,924 A | 1/1972 | Blake et al. | |
| 3,640,269 A | 2/1972 | Delgado | |
| 3,677,243 A | 7/1972 | Nerz | |
| 3,720,210 A | 3/1973 | Diettrich | |
| 3,812,851 A | 5/1974 | Rodriguez | |
| 3,826,257 A | 7/1974 | Buselmeier | |
| 3,890,977 A | 6/1975 | Wilson | |
| 3,921,631 A | 11/1975 | Thompson | |
| 3,935,857 A | 2/1976 | Co | |
| 3,942,528 A | 3/1976 | Loeser | |
| 3,964,488 A | 6/1976 | Ring et al. | |
| 3,983,203 A | 9/1976 | Corbett | |
| 3,998,222 A | 12/1976 | Shihata | |
| 4,016,879 A | 4/1977 | Mellor | |
| 4,020,823 A | 5/1977 | Baumbach | |
| 4,020,829 A | 5/1977 | Willson et al. | |
| 4,027,659 A | 6/1977 | Slingluff | |
| 4,027,668 A | 6/1977 | Dunn | |
| 4,033,331 A | 7/1977 | Guss et al. | |
| 4,079,737 A | 3/1978 | Miller | |
| 4,099,528 A | 7/1978 | Sorenson et al. | |
| 4,117,836 A | 10/1978 | Erikson | |
| 4,134,402 A | 1/1979 | Mahurkar | |
| 4,180,068 A | 12/1979 | Jacobsen et al. | |
| 4,202,332 A | 5/1980 | Tersteegen et al. | |
| 4,203,436 A | 5/1980 | Grimsrud | |
| 4,217,895 A | 8/1980 | Sagae et al. | |
| 4,220,813 A | 9/1980 | Kyle | |
| 4,220,814 A | 9/1980 | Kyle et al. | |
| 4,250,880 A | 2/1981 | Gordon | |
| 4,270,535 A | 6/1981 | Bogue et al. | |
| 4,292,976 A | 10/1981 | Banka | |
| 4,300,550 A | 11/1981 | Gandi et al. | |
| 4,306,562 A | 12/1981 | Osborne | |
| 4,311,152 A | 1/1982 | Modes et al. | |
| 4,352,354 A | 10/1982 | Ujihara | |
| 4,352,951 A | 10/1982 | Kyle | |
| 4,385,631 A | 5/1983 | Uthmann | |
| 4,392,855 A | 7/1983 | Oreopoulos et al. | |
| 4,402,685 A | 9/1983 | Buhler et al. | |
| 4,403,983 A | 9/1983 | Edelman et al. | |
| 4,405,313 A | 9/1983 | Sisley et al. | |
| 4,406,042 A | 9/1983 | McPhee | |
| 4,417,888 A | 11/1983 | Cosentino et al. | |
| D272,651 S | 2/1984 | Mahurkar | |
| 4,451,252 A | 5/1984 | Martin | |
| 4,451,256 A | 5/1984 | Weikl et al. | |
| 4,471,778 A | 9/1984 | Toye | |
| 4,493,696 A | 1/1985 | Uldall | |
| 4,508,535 A | 4/1985 | Joh et al. | |
| 4,531,933 A | 7/1985 | Norton et al. | |
| 4,543,087 A | 9/1985 | Sommercorn et al. | |
| 4,549,879 A | 10/1985 | Groshong et al. | |
| 4,557,261 A | 12/1985 | Rugheimer | |
| 4,563,180 A | 1/1986 | Jervis et al. | |
| 4,568,329 A | 2/1986 | Mahurkar | |
| 4,568,338 A | 2/1986 | Todd | |
| 4,576,199 A | 3/1986 | Svensson et al. | |
| 4,581,012 A | 4/1986 | Brown et al. | |
| 4,583,968 A | 4/1986 | Mahurkar | |
| 4,595,005 A | 6/1986 | Jinotti | |
| 4,596,559 A | 6/1986 | Fleischhacker | |
| 4,619,643 A | 10/1986 | Bai | |
| 4,623,327 A | 11/1986 | Mahurkar | |
| 4,626,240 A | 12/1986 | Edelman et al. | |
| 4,643,711 A | 2/1987 | Bates | |
| 4,648,868 A | 3/1987 | Hardwick et al. | |
| 4,668,221 A | 5/1987 | Luther | |
| 4,671,796 A | 6/1987 | Groshong et al. | |
| 4,675,004 A | 6/1987 | Hadford et al. | |
| 4,681,564 A | 7/1987 | Landreneau | |
| 4,681,570 A | 7/1987 | Dalton | |
| 4,682,978 A | 7/1987 | Martin | |
| 4,687,471 A | 8/1987 | Twardowski et al. | |
| 4,687,741 A | 8/1987 | Farrell et al. | |
| 4,692,141 A | 9/1987 | Mahurkar | |
| 4,694,838 A | 9/1987 | Wijayarthna et al. | |
| 4,701,159 A | 10/1987 | Brown et al. | |
| 4,701,166 A | 10/1987 | Groshong et al. | |
| 4,735,620 A | 4/1988 | Ruiz | |
| 4,738,667 A | 4/1988 | Galloway | |
| 4,739,768 A | 4/1988 | Engelson | |
| 4,772,268 A | 9/1988 | Bates | |
| 4,772,269 A | 9/1988 | Twardowski et al. | |
| 4,773,431 A | 9/1988 | Lodomirski | |
| 4,784,639 A | 11/1988 | Patel | |
| 4,789,000 A | 12/1988 | Aslanian | |
| 4,790,809 A | 12/1988 | Kuntz | |
| 4,795,439 A | 1/1989 | Guest | |
| 4,808,155 A | 2/1989 | Mahurkar | |
| 4,808,156 A | 2/1989 | Dean | |
| 4,820,349 A | 4/1989 | Saab | |
| 4,822,345 A | 4/1989 | Danforth | |
| 4,834,709 A | 5/1989 | Banning et al. | |
| 4,842,582 A | 6/1989 | Mahurkar | |
| 4,846,814 A | 7/1989 | Ruiz | |
| 4,867,742 A | 9/1989 | Calderon | |
| 4,883,058 A | 11/1989 | Ruiz | |
| 4,895,561 A | 1/1990 | Mahurkar | |
| 4,898,669 A | 2/1990 | Tesio | |
| 4,909,787 A | 3/1990 | Danforth | |
| 4,923,061 A * | 5/1990 | Trombley, III | A61M 25/002 206/439 |
| 4,935,004 A | 6/1990 | Cruz | |
| 4,961,731 A | 10/1990 | Bodicky et al. | |
| 4,961,809 A | 10/1990 | Martin | |
| 4,973,306 A | 11/1990 | Ruiz | |
| 4,976,703 A | 12/1990 | Franetzki et al. | |
| 4,981,477 A | 1/1991 | Schon et al. | |
| 4,985,014 A | 1/1991 | Orejola | |
| 4,995,872 A | 2/1991 | Ferrara | |
| 5,015,230 A | 5/1991 | Martin et al. | |
| 5,016,640 A | 5/1991 | Ruiz | |
| 5,041,083 A | 8/1991 | Tsuchida et al. | |
| 5,041,107 A | 8/1991 | Heil, Jr. | |
| 5,045,072 A | 9/1991 | Castillo et al. | |
| 5,053,003 A | 10/1991 | Dadson et al. | |
| 5,053,004 A | 10/1991 | Markel et al. | |
| 5,053,023 A | 10/1991 | Martin | |
| 5,057,073 A | 10/1991 | Martin | |
| 5,058,595 A | 10/1991 | Kern | |
| 5,084,024 A | 1/1992 | Skinner | |
| 5,098,413 A | 3/1992 | Trudell et al. | |
| 5,141,499 A | 8/1992 | Zappacosta | |
| 5,156,592 A | 10/1992 | Martin et al. | |
| 5,171,216 A | 12/1992 | Dasse et al. | |
| 5,171,227 A | 12/1992 | Fwardowski et al. | |
| 5,186,715 A | 2/1993 | Phillips et al. | |
| 5,188,619 A | 2/1993 | Myers | |
| 5,197,951 A | 3/1993 | Mahurkar | |
| 5,209,723 A | 5/1993 | Fwardowski et al. | |
| 5,221,255 A | 6/1993 | Mahurkar et al. | |

(56) References Cited

U.S. PATENT DOCUMENTS

| | | |
|---|---|---|
| 5,221,256 A | 6/1993 | Mahurkar |
| 5,292,305 A | 3/1994 | Boudewijn et al. |
| 5,306,263 A | 4/1994 | Voda |
| 5,318,588 A | 6/1994 | Horzewski et al. |
| 5,324,274 A | 6/1994 | Martin |
| 5,327,905 A | 7/1994 | Avitall |
| 5,346,471 A | 9/1994 | Raulerson |
| 5,350,358 A | 9/1994 | Martin |
| 5,354,271 A | 10/1994 | Voda |
| 5,354,297 A | 10/1994 | Avitall |
| 5,358,479 A | 10/1994 | Wilson |
| 5,358,493 A | 10/1994 | Schweich, Jr. et al. |
| 5,374,245 A | 12/1994 | Mahurkar |
| 5,380,276 A | 1/1995 | Miller et al. |
| 5,395,316 A | 3/1995 | Martin |
| 5,401,258 A | 3/1995 | Voda |
| 5,403,291 A | 4/1995 | Abrahamson |
| 5,405,320 A | 4/1995 | Twardowski et al. |
| 5,405,341 A | 4/1995 | Martin |
| 5,443,460 A | 8/1995 | Miklusek |
| 5,445,625 A | 8/1995 | Voda |
| 5,507,995 A | 4/1996 | Schweich, Jr. et al. |
| 5,509,897 A | 4/1996 | Twardowski et al. |
| 5,509,902 A | 4/1996 | Raulerson |
| 5,569,182 A | 10/1996 | Fwardowski et al. |
| 5,569,197 A | 10/1996 | Helmus et al. |
| 5,569,218 A | 10/1996 | Berg |
| 5,599,311 A | 2/1997 | Raulerson |
| 5,603,704 A | 2/1997 | Brin et al. |
| 5,624,413 A | 4/1997 | Markel et al. |
| 5,650,759 A | 7/1997 | Hittman et al. |
| 5,685,867 A | 11/1997 | Twardowski et al. |
| 5,718,678 A | 2/1998 | Fleming, III |
| 5,718,692 A | 2/1998 | Schon et al. |
| 5,741,233 A | 4/1998 | Riddle et al. |
| 5,755,760 A | 5/1998 | Maguire et al. |
| 5,776,111 A | 7/1998 | Tesio |
| 5,795,326 A | 8/1998 | Siman |
| 5,830,184 A | 11/1998 | Basta |
| 5,830,196 A | 11/1998 | Hicks |
| 5,868,700 A | 2/1999 | Moda |
| 5,885,259 A | 3/1999 | Berg |
| 5,897,537 A | 4/1999 | Berg et al. |
| 5,902,282 A | 5/1999 | Balbierz |
| 5,916,199 A | 6/1999 | Miles |
| 5,931,829 A | 8/1999 | Burbank et al. |
| 5,941,872 A | 8/1999 | Berg |
| 5,944,732 A | 8/1999 | Raulerson et al. |
| 5,947,284 A | 9/1999 | Foster |
| 5,947,931 A | 9/1999 | Bierman |
| 5,947,953 A | 9/1999 | Ash et al. |
| 5,957,961 A | 9/1999 | Maguire et al. |
| 5,961,486 A | 10/1999 | Twardowski et al. |
| 5,968,009 A | 10/1999 | Siman |
| 5,989,206 A | 11/1999 | Prosl et al. |
| 5,989,213 A | 11/1999 | Maginot |
| 6,001,079 A | 12/1999 | Pourchez |
| 6,001,081 A | 12/1999 | Collen |
| 6,002,955 A | 12/1999 | Willems et al. |
| 6,004,280 A | 12/1999 | Buck et al. |
| 6,024,693 A | 2/2000 | Schock et al. |
| 6,033,382 A | 3/2000 | Basta |
| 6,083,213 A | 7/2000 | Voda |
| 6,105,218 A | 8/2000 | Reekie |
| 6,110,163 A | 8/2000 | Voda |
| 6,120,495 A | 9/2000 | Voda |
| 6,156,016 A | 12/2000 | Maginot |
| 6,190,349 B1 | 2/2001 | Ash et al. |
| 6,190,371 B1 | 2/2001 | Maginot et al. |
| 6,277,100 B1 | 8/2001 | Raulerson et al. |
| 6,280,423 B1 | 8/2001 | Davey et al. |
| 6,293,927 B1 | 9/2001 | McGuckin, Jr. |
| 6,342,120 B1 | 1/2002 | Basta |
| 6,356,790 B1 | 3/2002 | Maguire et al. |
| 6,475,195 B1 | 11/2002 | Voda |
| 6,475,207 B1 | 11/2002 | Maginot et al. |
| 6,533,763 B1 | 3/2003 | Schneiter |
| 6,551,281 B1 | 4/2003 | Raulerson et al. |
| 6,558,368 B1 | 5/2003 | Voda |
| 6,585,705 B1 | 7/2003 | Maginot et al. |
| 6,595,966 B2 | 7/2003 | Davey et al. |
| 6,595,983 B2 | 7/2003 | Voda |
| 6,620,118 B1 | 9/2003 | Prosl et al. |
| 6,638,242 B2 | 10/2003 | Wilson et al. |
| 6,682,519 B1 | 1/2004 | Schon |
| 6,695,832 B2 | 2/2004 | Schon et al. |
| 6,719,749 B1 | 4/2004 | Schweikert et al. |
| 6,723,084 B1 | 4/2004 | Maginot et al. |
| D489,452 S | 5/2004 | Schweikert |
| 6,730,096 B2 | 5/2004 | Basta |
| D491,265 S | 6/2004 | Schweikert |
| 6,743,218 B2 | 6/2004 | Maginot et al. |
| 6,749,580 B2 | 6/2004 | Work et al. |
| 6,796,991 B2 | 9/2004 | Nardeo |
| D498,299 S | 11/2004 | Schweikert |
| 6,814,718 B2 | 11/2004 | McGuckin, Jr. et al. |
| 6,823,617 B2 | 11/2004 | Schweikert |
| 6,858,019 B2 | 2/2005 | McGuckin, Jr. et al. |
| 6,881,211 B2 | 4/2005 | Schweikert et al. |
| D505,202 S | 5/2005 | Chesnin |
| 6,911,014 B2 | 6/2005 | Wentling et al. |
| 6,916,051 B2 | 7/2005 | Fisher |
| 6,926,669 B1 | 8/2005 | Stewart et al. |
| 6,926,721 B2 | 8/2005 | Basta |
| 6,939,328 B2 | 9/2005 | Raulerson |
| 6,969,381 B2 | 11/2005 | Voorhees |
| 6,986,752 B2 | 1/2006 | McGuckin, Jr. et al. |
| 6,991,625 B1 | 1/2006 | Gately et al. |
| D515,211 S | 2/2006 | Chesnin |
| 7,008,412 B2 | 3/2006 | Maginot |
| 7,011,645 B2 | 3/2006 | McGuckin, Jr. et al. |
| 7,018,374 B2 | 3/2006 | Schon et al. |
| 7,066,925 B2 | 6/2006 | Gately et al. |
| D525,359 S | 7/2006 | Stephens |
| 7,074,213 B2 | 7/2006 | McGuckin, Jr. et al. |
| 7,077,829 B2 | 7/2006 | McGuckin, Jr. et al. |
| D530,420 S | 10/2006 | Chesnin |
| 7,115,134 B2 | 10/2006 | Chambers |
| 7,163,531 B2 | 1/2007 | Seese et al. |
| 7,172,571 B2 | 2/2007 | Moskowitz et al. |
| 7,220,246 B2 | 5/2007 | Raulerson et al. |
| 7,223,263 B1 | 5/2007 | Seno |
| D544,600 S | 6/2007 | Wentling |
| D546,446 S | 7/2007 | Chesnin |
| 7,261,708 B2 | 8/2007 | Raulerson |
| 7,393,339 B2 | 7/2008 | Zawacki et al. |
| 7,494,478 B2 | 2/2009 | Itou et al. |
| 7,695,450 B1 | 4/2010 | Twardowski et al. |
| 7,799,013 B2 | 9/2010 | Gandras |
| 7,867,218 B1 | 1/2011 | Voda |
| 7,976,518 B2 | 7/2011 | Shaughnessy et al. |
| 8,021,321 B2 | 9/2011 | Zawacki |
| 8,029,457 B2 | 10/2011 | Ash et al. |
| 8,066,660 B2 | 11/2011 | Gregersen et al. |
| 8,092,415 B2 | 1/2012 | Moehle et al. |
| 8,152,951 B2 | 4/2012 | Zawacki et al. |
| 8,206,371 B2 | 6/2012 | Nimkar et al. |
| 8,292,841 B2 | 10/2012 | Gregersen |
| 8,323,227 B2 | 12/2012 | Hamatake et al. |
| 8,409,191 B2 | 4/2013 | Avitall et al. |
| 8,500,939 B2 | 8/2013 | Nimkar et al. |
| 8,540,661 B2 | 9/2013 | Gregersen |
| 8,597,275 B2 | 12/2013 | Nimkar et al. |
| 8,696,614 B2 | 4/2014 | Gregersen et al. |
| 8,808,227 B2 | 8/2014 | Zawacki et al. |
| 8,827,943 B2 | 9/2014 | Angheloiu et al. |
| 8,876,754 B2 | 11/2014 | Ranchod et al. |
| 8,894,601 B2 | 11/2014 | Moehle et al. |
| 8,992,454 B2 | 3/2015 | Anand |
| 9,126,011 B2 | 9/2015 | Ash et al. |
| 9,131,956 B2 | 9/2015 | Shaughnessy et al. |
| 9,155,860 B2 | 10/2015 | Ash et al. |
| 9,174,019 B2 | 11/2015 | Gregersen |
| 9,233,200 B2 | 1/2016 | Gregersen et al. |

(56) References Cited

U.S. PATENT DOCUMENTS

| | | |
|---|---|---|
| 9,492,634 B2 | 11/2016 | Moehle et al. |
| 2001/0014787 A1 | 8/2001 | Toyokawa et al. |
| 2002/0032411 A1 | 3/2002 | Basta |
| 2002/0091362 A1 | 7/2002 | Maginot et al. |
| 2002/0120224 A1 | 8/2002 | Zia et al. |
| 2002/0130059 A1 | 9/2002 | Armijo |
| 2003/0036698 A1 | 2/2003 | Kohler et al. |
| 2003/0066218 A1 | 4/2003 | Schweikert |
| 2003/0093027 A1 | 5/2003 | McGuckin et al. |
| 2003/0093029 A1 | 5/2003 | McGuckin et al. |
| 2003/0114832 A1 | 6/2003 | Kohler et al. |
| 2003/0144623 A1 | 7/2003 | Heath et al. |
| 2004/0015151 A1 | 1/2004 | Chambers |
| 2004/0034324 A1 | 2/2004 | Seese et al. |
| 2004/0034333 A1 | 2/2004 | Seese et al. |
| 2004/0054321 A1 | 3/2004 | Schon et al. |
| 2004/0059314 A1 | 3/2004 | Schon et al. |
| 2004/0075198 A1 | 4/2004 | Schweikert et al. |
| 2004/0092863 A1 | 5/2004 | Raulerson et al. |
| 2004/0097903 A1 | 5/2004 | Raulerson |
| 2004/0122416 A1 | 6/2004 | Schweikert et al. |
| 2004/0186461 A1 | 9/2004 | DiMatteo |
| 2004/0193098 A1 | 9/2004 | Wentling et al. |
| 2004/0195131 A1 | 10/2004 | Spolidoro |
| 2004/0249349 A1 | 12/2004 | Wentling |
| 2005/0000844 A1 | 1/2005 | Schweikert |
| 2005/0015007 A1 | 1/2005 | Itou et al. |
| 2005/0038453 A1 | 2/2005 | Raulerson |
| 2005/0043684 A1 | 2/2005 | Basta et al. |
| 2005/0049572 A1 | 3/2005 | Schweikert et al. |
| 2005/0049628 A1 | 3/2005 | Schweikert et al. |
| 2005/0054990 A1 | 3/2005 | Graft et al. |
| 2005/0085765 A1 | 4/2005 | Voorhees |
| 2005/0096580 A1 | 5/2005 | Moskowitz et al. |
| 2005/0096585 A1 | 5/2005 | Schon et al. |
| 2005/0096609 A1 | 5/2005 | Maginot et al. |
| 2005/0101903 A1 | 5/2005 | Kohler et al. |
| 2005/0107770 A1 | 5/2005 | Schweikert et al. |
| 2005/0113801 A1 | 5/2005 | Gandras |
| 2005/0120523 A1 | 6/2005 | Schweikert |
| 2005/0124970 A1 | 6/2005 | Kunin et al. |
| 2005/0137527 A1 | 6/2005 | Kunin |
| 2005/0137580 A1 | 6/2005 | Raulerson et al. |
| 2005/0192545 A1 | 9/2005 | Voorhees et al. |
| 2005/0209583 A1 | 9/2005 | Powers et al. |
| 2005/0222593 A1 | 10/2005 | Markel et al. |
| 2005/0234369 A1 | 10/2005 | Voorhees |
| 2005/0245900 A1 | 11/2005 | Ash |
| 2005/0261665 A1 | 11/2005 | Voorhees |
| 2006/0004316 A1 | 1/2006 | Difiore et al. |
| 2006/0004324 A1 | 1/2006 | Ruddell et al. |
| 2006/0015072 A1 | 1/2006 | Raulerson |
| 2006/0015130 A1 | 1/2006 | Voorhees et al. |
| 2006/0030827 A1 | 2/2006 | Raulerson et al. |
| 2006/0047267 A1 | 3/2006 | Gately et al. |
| 2006/0047268 A1 | 3/2006 | Stephens |
| 2006/0064072 A1 | 3/2006 | Gately et al. |
| 2006/0095030 A1 | 5/2006 | Avitall et al. |
| 2006/0095062 A1 | 5/2006 | Stephens |
| 2006/0184142 A1 | 8/2006 | Schon et al. |
| 2006/0189959 A1 | 8/2006 | Schneiter |
| 2006/0200111 A1 | 9/2006 | Moehle et al. |
| 2006/0206094 A1 | 9/2006 | Chesnin et al. |
| 2006/0253063 A1 | 11/2006 | Schweikert |
| 2006/0271012 A1 | 11/2006 | Canaud et al. |
| 2007/0043307 A1 | 2/2007 | Raulerson et al. |
| 2007/0049960 A1 | 3/2007 | Stephens et al. |
| 2007/0060866 A1 | 3/2007 | Raulerson et al. |
| 2007/0073271 A1 | 3/2007 | Brucker et al. |
| 2007/0135794 A1 | 6/2007 | Raulerson et al. |
| 2007/0198047 A1 | 8/2007 | Schon et al. |
| 2007/0219510 A1 | 9/2007 | Zinn et al. |
| 2007/0225661 A1 | 9/2007 | Ash et al. |
| 2007/0225682 A1 | 9/2007 | Ash et al. |
| 2007/0225683 A1 | 9/2007 | Raulerson et al. |
| 2007/0225684 A1 | 9/2007 | Wentling et al. |
| 2007/0233017 A1 | 10/2007 | Zinn et al. |
| 2007/0233018 A1 | 10/2007 | Bizup et al. |
| 2007/0233042 A1 | 10/2007 | Moehle et al. |
| 2008/0021417 A1 | 1/2008 | Zawacki et al. |
| 2008/0039774 A1 | 2/2008 | Zawacki et al. |
| 2008/0045886 A1 | 2/2008 | Hobbs et al. |
| 2008/0045894 A1 | 2/2008 | Perchik et al. |
| 2008/0082080 A1 | 4/2008 | Braga |
| 2008/0097339 A1 | 4/2008 | Ranchod et al. |
| 2009/0018493 A1 | 1/2009 | Ash et al. |
| 2009/0306574 A1 | 12/2009 | Kopperschmidt |
| 2014/0200524 A1 | 7/2014 | Wiley et al. |

FOREIGN PATENT DOCUMENTS

| | | |
|---|---|---|
| DE | 545218 C | 2/1932 |
| DE | 2627850 A1 | 1/1977 |
| DE | 2627851 C2 | 7/1984 |
| DE | 3736226 A1 | 5/1989 |
| DK | 146777 B | 1/1984 |
| EP | 0036642 A2 | 9/1981 |
| EP | 0102342 A2 | 3/1984 |
| EP | 0132344 A2 | 1/1985 |
| EP | 0081724 B1 | 3/1986 |
| EP | 0242985 A2 | 10/1987 |
| EP | 0263645 A2 | 4/1988 |
| EP | 323738 A2 | 7/1989 |
| EP | 0386408 A1 | 9/1990 |
| EP | 386408 A1 | 9/1990 |
| EP | 256478 B1 | 1/1992 |
| ES | 2069287 T3 | 5/1995 |
| FR | 2529083 B2 | 4/1987 |
| GB | 2238724 A | 6/1991 |
| JP | 59034265 | 2/1984 |
| JP | 63111833 | 5/1988 |
| JP | 1058263 A | 3/1989 |
| JP | 1238872 | 9/1989 |
| WO | 1991015255 | 10/1991 |
| WO | 1992012754 | 8/1992 |
| WO | 1993021983 | 11/1993 |
| WO | 1996024399 A1 | 8/1996 |
| WO | 1997017102 | 5/1997 |
| WO | 2000023137 A1 | 4/2000 |
| WO | 02/13899 A1 | 2/2002 |
| WO | 2002030489 A2 | 4/2002 |
| WO | 2003030960 A2 | 4/2003 |

OTHER PUBLICATIONS

Medcomp; Effective Solutions for Vascular Access; Product Line; Dialysis and Vascular Access products Brochure. Rev. D; (Apr. 2006).

Medcomp; Hemodialysis Products; Product line. (Date unknown).

Netter, Frank H.; A compilation of Paintings on the Normal and Pathologic Anatomy and Physiology, Embryology, and Diseases of the Heart; The Ciba Collection of Medical Illustrations, vol. 5. Section I—Plate 5. (1969).

Ota et al. "A Completely New Poly(ether-urethane) Graft Ideal for Hemodialysis Blood Access." Trans Am Soc Artif Intem Organs, vol. XXXIII, pp. 129-135, 1987.

Palmer, Russell A, et al., "Prolonged Peritoneal Dialysis for Chronic Renal Failure," The Lancet, Mar. 28, 1964.

Palmer, Russell A., "Treatment of Chronic Renal Failure by Prolonged Peritoneal Dialysis." The New England Journal of Medicine, vol. 274, No. 5, Feb. 3, 1966.

PCT/US2007/008148 filed Apr. 2, 2007 International Preliminary Report on Patentability dated Sep. 30, 2008.

PCT/US2007/008148 filed Apr. 2, 2007 Search Report dated Aug. 28, 2007.

PCT/US2007/008148 filed Apr. 2, 2007 Written Opinion dated Aug. 28, 2007.

Peters, Joseph L., et al., "Long-term venous access." British Journal of Hospital Medicine, 1984.

Pristave, Robert J., "Medicare Audits." Dialysis & Transplantation, vol. 12, No. 7, Jul. 1983.

(56) References Cited

OTHER PUBLICATIONS

Quinton et al. "Eight Months' Experience with Silastic-Teflon Bybass Cannulas," Department of Medicine and Surgery, University of Washington and the Quinton Instrument Company, 1961.
Quinton Instrument Co; Descriptions and Instructions for use of PermCath HemoCath Dual Lumen Catheter; 1984.
Quinton Instrument Company; Peritoneal Dialysis and Hemodialysis; Catalog. (Date unknown).
Quinton; PermCath and Pediatric PermCath Catheters; Instructions for Use. (Date unknown).
Raja et al. "Comparison of Double Lumen Subclavian with Single Lumen Catheter—One Year Experience." Trans American Society of Artificial Internal Organs, vol. XXX 1984.
Ratcliffe, P.J. et al., "Massive Thrombosis around Subclavian Cannulas Used for Haemodialysis" The Lancet (Letters to the Editor), vol. 1, No. 8287, 1982.
Saklayen, "Letters to the editor re: prolonged use of a Subclavian Catheter for Hemodialysis." Dialysis & Transplantation, Apr. 1998.
Sanders et al. "Experience with Double Lumen Right Atrial Catheters." American Society of Parenteral and Enteral Nutrition, vol. 6, No. 2 , pp. 95-99, 1982.
Schillinger, F., et al., "Post Catheterisation Vein Stenosis in Haemodialysis: Comparative Angiographic Study of 50 Subclavian and 50 Internal Jugular Accesses", Nephrology Dialysis Transplantation, vol. 6, No. 10, 1991.
Scribner et al. "Evolution of the Technique of Home Parenteral Nutrition." Journal of Parenteral and Enteral Nutrition. vol. 3, No. 2, pp. 58-61, 1979.
Seldinger, Sven Irar, "Catheter Replacement of the Needle in Percutaneous Arteriography." Roentgen Diagnostic Department, Karolnska Sjukhuset, Stockholm, Sweden. May, 1, 1953.
Shaldon, Stanley, et al., "Hemodialysis by Percutaneous Cathererisation of the Femoral Artery and Vein with Regional Heparinisation." The Lancet, vol. 2, 1961.
Shaldon, Stanley, et al., "New Developments with Artificial Kidney." British Medical Journal, London, Jun. 29, 1963.
Shiley; Subclavian Cannulae; Aug. 1986.
Shiley© "Major Improvement. Major Advantage. Shiley's All-Silicone Subclavian Cannual." Brochure, 1980.
Shileyó; Subclavian Cannulae product brochure, 1986.
Sims, Terran W., et al., "Successful Utilization of Subclavian Catheters for Hemodialysis and Apheresis Access", AANNT Journal, vol. 10, No. 6, 1993.
Twardowski, Zbylut J., "Chapter 57: Peritoneal Catheter Placement and Management." Suki and Massry's Therapy of Renal Diseases and Related Disorders, Third Edition, pp. 953-979. (1998).
Twardowski, Zbylut J., "The Need for a 'Swan-Neck' Permantently Bent Arcuate Peritoneal Dialysis Catheter." Peritoneal Dialysis Bulletin, Oct.-Dec. 1985.
Uldall, P.R., et al., "A Subclavian Cannula for Temporary Vascular Access for Hemodialysis of Plasmapheresis." Dialysis & Transplantation, vol. 8, No. 10, p. 963, 1979.
U.S. Appl. No. 11/732,030, filed Apr. 2, 2007 Final Office Action dated Jul. 24, 2013.
U.S. Appl. No. 11/732,030, filed Apr. 2, 2007 Non-Final Office Action dated Jun. 14, 2012.
U.S. Appl. No. 11/732,030, filed Apr. 2, 2007 Advisory Action dated Jun. 4, 2010.
U.S. Appl. No. 11/732,030, filed Apr. 2, 2007 Final Office Action dated Jan. 8, 2009.
U.S. Appl. No. 11/732,030, filed Apr. 2, 2007 Final Office Action dated Mar. 23, 2010.
U.S. Appl. No. 11/732,030, filed Apr. 2, 2007 Final Office Action dated Sep. 18, 2012.
U.S. Appl. No. 11/732,030, filed Apr. 2, 2007 Non-Final Office Action dated Apr. 2, 2008.
U.S. Appl. No. 11/732,030, filed Apr. 2, 2007 Non-Final Office Action dated Aug. 20, 2009.
U.S. Appl. No. 11/732,030, filed Apr. 2, 2007 Non-Final Office Action dated Dec. 3, 2012.
U.S. Appl. No. 14/152,599, filed Jan. 10, 2014 Advisory Action dated Nov. 24, 2017.
U.S. Appl. No. 14/152,599, filed Jan. 10, 2014 Non-Final Action dated Mar. 29, 2018.
U.S. Appl. No. 14/152,599, filed Jan. 10, 2014 Non-Final Office Action dated Feb. 13, 2017.
U.S. Appl. No. 14/152,599, filed Jan. 10, 2014 Notice of Allowance dated Nov. 28, 2018.
Vanherweghem et al. "Complications Related to Subclavian Catheters for Hemodialysis." American Journal of Nephrol 6, pp. 339-345, 1986.
Vas-Cath, "Go for the Jugular" temporary catheter product advertisement, 1994.
Vas-Cath, "Uldallä SC-100 Means Quality" Advertisement, 1980.
Vas-Cath; Accessories/Price List for Canadian Hospitals, Hemodialysis Products effecive May 1, 1982.
Vas-Cath; Accessories/Price List. (1982).
Vas-Cath; Catheter Repair Kit CRK-1 with Titanium Replacement Connector; 1988.
Vas-Cath; Confidential Training Manual and Marketing Support File for Vascular Access Catheters and Accessories tor Dialysis; Revised Jan. 1989.
Vas-Cath; Flexxicon Dual Lumen Catheters. Instructions for Use distributed by Vas-Cath. (1988).
Vas-Cath; For acute dialysis . . . Vas-Cath is accessible; Advertistement; 1987.
Vas-Cath; Instructions for use of Flexxicon Dual Lumen Catheters (DLC), Kits (DLK), Trays (DLT); 1988.
Vas-Cath; Instructions for use of Soft-cell Permanent Dual Lumen Catheter; May 25, 1998.
Vas-Cath; Niagara, Dual Lumen Catheter Instructions for Use; Jun. 1997; Canada.
Vas-Cath; Opti-Flow and Soft-Cell; Dual Lumen Catheter Straight and Pre-Curved (PC) Catheters, with and without VitaCuff; Jun. 16, 1997.
Vas-Cath; Peritoneal Dialysis Catheters; Indications for use; 1988.
Vas-Cath; Permanent Dual Lumen Catheter for Vas-Cath; Advertisement; Contemporary Dialysis and Nephrology, May 1988.
Vas-Cath; Single Lumen PTFE SubClavian/Femoral Cannulas, Sc-100; Advertisement. (Date unknown).
Vas-Cath; Soft-cell Permanent Dual Lumen Cannula with Dacron Cuff; Product details; 1988.
Vas-Cath; Soft-Cell Permanent Dual Lumen Catheter; Insertion Guide. (1989).
Vas-Cath; Temporary Vascular Access Products. (1985).
Vas-Cath; Temporary Vascular Access Products; Product Line; 1985.
Vas-Cath; The Vas-Cath Advantage: Temporary and Permanent Dual Lumen Catheters, Flexxicon® & Flexxicon® Blue brochure. (Date unknown).
Vas-Cath; Vaccess 1000 Series Single Lumen Femoral Cannulas (Hemodialysis); 1984.
Vas-Cath; Vaccess 2 Double-Lumen Subclavian Cannula. (1982).
Vas-Cath; Vaccess 2000 Series Single Lumen Subclavian Cannulas (Central Venous Access/Hemodialysis). Brochure distributed by Vas-Cath. (1984).
Vas-Cath; Vaccess 2000 Series Single Lumen Subclavian Cannulas (Single Needle Hemodialysis); 1984.
Vas-Cath; Vaccess 2000: Single Lumen Subclavian Cannulas, Instructions for Use—Central Venous Access. (1984).
Vas-Cath; Vaccess 2000: Single Lumen Subclavian Cannulas, Instructions for Use—Single Needle Hemodialysis. (1984).
Young, Warren, "Chapter 14: Elastic Stability". Roark's Formulas for Stress Strain 1989.
Zuniga et al. "Hemodialisis: Accesso Vascular Con Cateter De Doble Lumen." Rev. Med. Chile; 117: pp. 991-996, 1989.
Annest, Lon S et al. "Use of a Split-Sheath Vein Introducer for Subclavian Venipuncture in the Placement of Silicone Catheters for Chronic Venous Access." The American Journal of Surgery, vol. 144, pp. 367-369, 1982.
Aubaniac, Robert. "L'injection intraveineuse sous-claviculaire: Avantages et technique." La Presse Medicale. 1952.

(56) References Cited

OTHER PUBLICATIONS

Bard Access Systems; HemoSplit Long-Term Hemodialysis Catheter, Instructions for Use; Apr. 2003.
Bard Access Systems; Power Picc The Universal Picc, Polyurethane PICC with Safety Excalibur Introducer System Instructions for Use; Jul. 2003.
Bard Access Systems; PowerPicc, The Universal Picc, Polyurethane Radiology Catheters with Microintroducer Set Instructions for Use; Nov. 2003.
Bard; 135cm Guidewire, Instructions for Use; Mar. 2002, excerpt.
Bard; HemoGlide Long Term Hemodialysis Catheter Instructions for Use for HemoGlide Straight and Precurved (PC) Catheters, with and without VitaCuffÓ Antimicrobial Cuff, 2002.
Berlyne, G.M., "Editorial: Hemodialysis versus the Newer Techniques." Nephron, vol. 27, No. 1, 1981.
Bregman, Harold, et al., "Minimum Performance Standards for Double-Lumen Subclavian Cannulas for Hemodialysis." vol. 32, No. 1, 1986.
Bregman, Harold, et al.,"The Double-Lumen Subclavian Cannula—A Unique Concept in Vascular Access". Dialysis & Transplantation, vol. 11, No. 12, pp. 1065-1070, 1982.
Bricker, Catherine., "Psychosocial Implications of Nutrition Assessment for Adult Chronic Renal Failure Patients." Dialysis & Transplantation, vol. 11, No. 5, May 1982.
Carbone, Vera, "Hemodialysis Using the PermCath Double Lumen Catheter." ANNA Journal, vol. 15, No. 3, pp. 171-173, 1988.
Cheesbrough et al. "A Prospective Study of the Mechanisms of Infection Associated with Hemodialysis Catheters." The Journal of Infectious Diseases vol. 154, No. 4, pp. 579-589, 1986.
Cimochowski, George E., et al., "Superiority of the Internal Jugular over teh Subclavian Access for Temporary Dialysis." Nephron, vol. 54, No. 2, 1990.
Cook Critical Care; Cook TPN Pre-Cut Double Lumen Catheters with Off-Set Tips; A000053 1982.
Cook Incorporated; Subclavian Double Lumen Hemodialysis Sets and Trays; Patent No. 4,306,562. (Date unknown).
Cournand et al. "Double Lumen Catheter for Intravenous and Intracardiac Blood Sampling and Pressure Recording." Proceedings of the Society for Experimental Biology and Medicine, vol. 60, pp. 73, 1994.
Dialysis & Transplantation (A creative Age Publication); vol. 11 No. 6, Jun. 1982. pp. 538-541 & 554.
Dialysis & Transplantation (A creative Age Publication); vol. 13, No. 8, Aug. 1984. pp. 517-520 & 544.
Dialysis & Transplantation; vol. 11, No. Aug. 1982. pp. 669-677 & 730.
Dialysis & Transplantation; vol. 11, No. 9, Sep. 1982. pp. 787-790 & 832.
Dialysis & Transplantation; vol. 11, No. 11, Nov. 1982. pp. 1007-1011 & 1032.
Dialysis & Transplantation; vol. 11, No. 12, Dec. 1982. pp. 1064-1070, 1081-1085, & 1134.
Dialysis & Transplantation; vol. 11, No. 7, Jul. 1982. pp. 618-621 & 638.
Dialysis & Transplantation; vol. 12, No. 1, Jan. 1983. pp. 20-24 & 68.
Dialysis & Transplantation; vol. 12, No. 2, Feb. 1983. pp. 119-122 & 144.
Dialysis & Transplantation; vol. 12, No. 3, Mar. 1983. pp. 166-167, 185-190, & 206.
Dialysis & Transplantation; vol. 12, No. 4, Apr. 1983. pp. 295-303, 318.
Dialysis & Transplantation; vol. 12, No. 5, May 1983. pp.327-328, 330-339, 346-351, 404.
Dialysis & Transplantation; vol. 12, No. 6, Jun. 1983. pp. 459-464, 482.
Dialysis & Transplantation; vol. 12, No. 7, Jul. 1983. pp. 495-501, 544.
Dialysis & Transplantation; vol. 12, No. 8, Aug. 1983. pp. 567-572, 604.
Dialysis & Transplantation; vol. 12, No. 9, Sep. 1983. pp. 673-676, 678.
Dialysis & Transplantation; vol. 13, No. 10, Oct. 1984. pp. 637-640, 680.
Dialysis & Transplantation; vol. 13, No. 5, May 1984. pp. 297-300, 303, 322-328, 332.
Dialysis & Transplantation; vol. 13, No. 6, Jun. 1984. pp. 345-354, 396-398, 404.
Dialysis & Transplantation; vol. 13, No. 7, Jul. 1984. pp. 443-446, 464-466, 496.
Dialysis & Transplantation; vol. 13, No. 8, Aug. 1984. pp. 543-544, 518-520.
Dialysis & Transplantation; vol. 13, No. 9, Sep. 1984. pp. 562-570, 608.
Dialysis & Transplantation; vol. 14, No. 3, Mar. 1985. pp. 122-124, 165-169, 178.
Dialysis & Transplantation; vol. 14, No. 5, May 1985. pp. 264-270, 304-306, 310.
Dialysis & Transplantation; vol. 17, No. 6, Jun. 1988. pp. 279-282, 321.
Dufy, B. J. "The Clinical Use of Polyethylene Tubing for Intravenous Therapy." Annals of Surgery, vol. 136, No. 5, 1949.
Dunn, John, et al., "Centra venous dialysis access: Experience with a dual-lumen, silicone rubber catheter." Surgery, vol. 102, No. 5, Nov. 1987.
Erben, Joseph, et al., "Experience with Routine use of Subclavian Vein Cannulation in Haemodialysis." Dialysis and Renal Transplantation, vol. 6, 1969.
Hickman, Robert O., et al., "A Review of Hemodialysis Catheters and Access Devices." Dialysis & Transplantation, vol. 16, No. 9, pp. 481 485, 1997.
Hoshal, Verne L., et al., "Fibrin Sleeve Formation on Indwelling Subclavian Central Venous Catheters." Archives of Surgery, vol. 102, 1971.
Impra; Dual Lumen Subclavian Catheter; Information, (date unknown).
Lally et al. "Use of Subclavian Venous Catheter for Short- and Long-term Hemodialysis in Children." Journal of Pediatric Surgery, vol. 44, No. 7, pp. 603-605, 1987.
McDowell, Donald E., et al., "A Simplified technique for percutaneous insertion of permanenet vascular access catheters in patients requiring chronic hemodialysis." Section of Vascular Surgery, Department of Surgery, West Virginia University Medical Center, Morgantown, WV 26505. (1988).

* cited by examiner

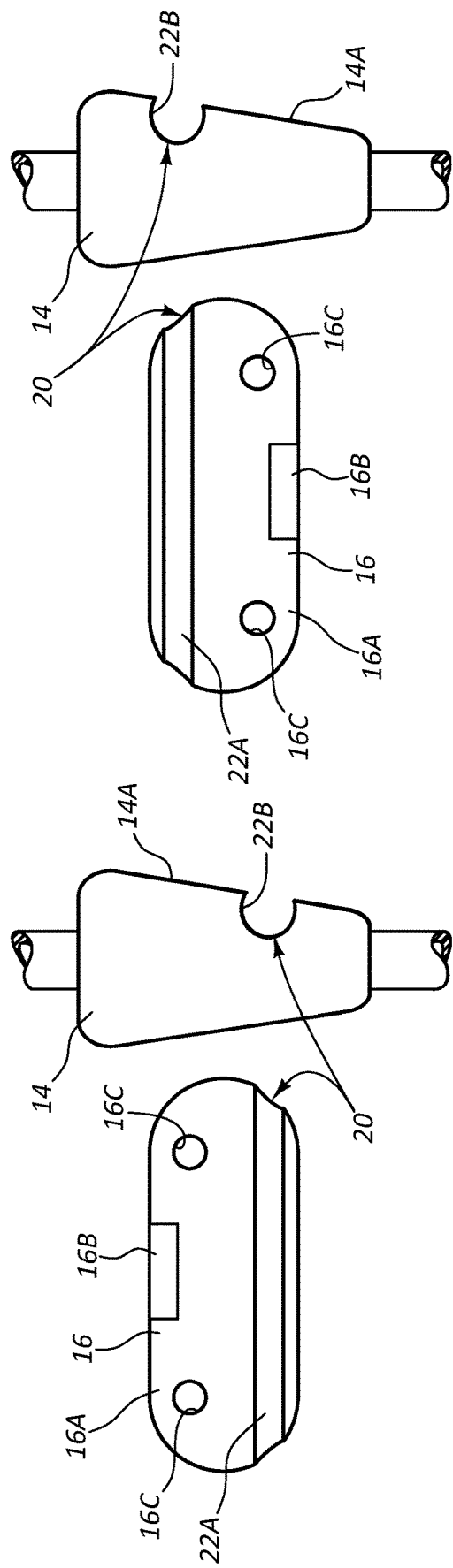

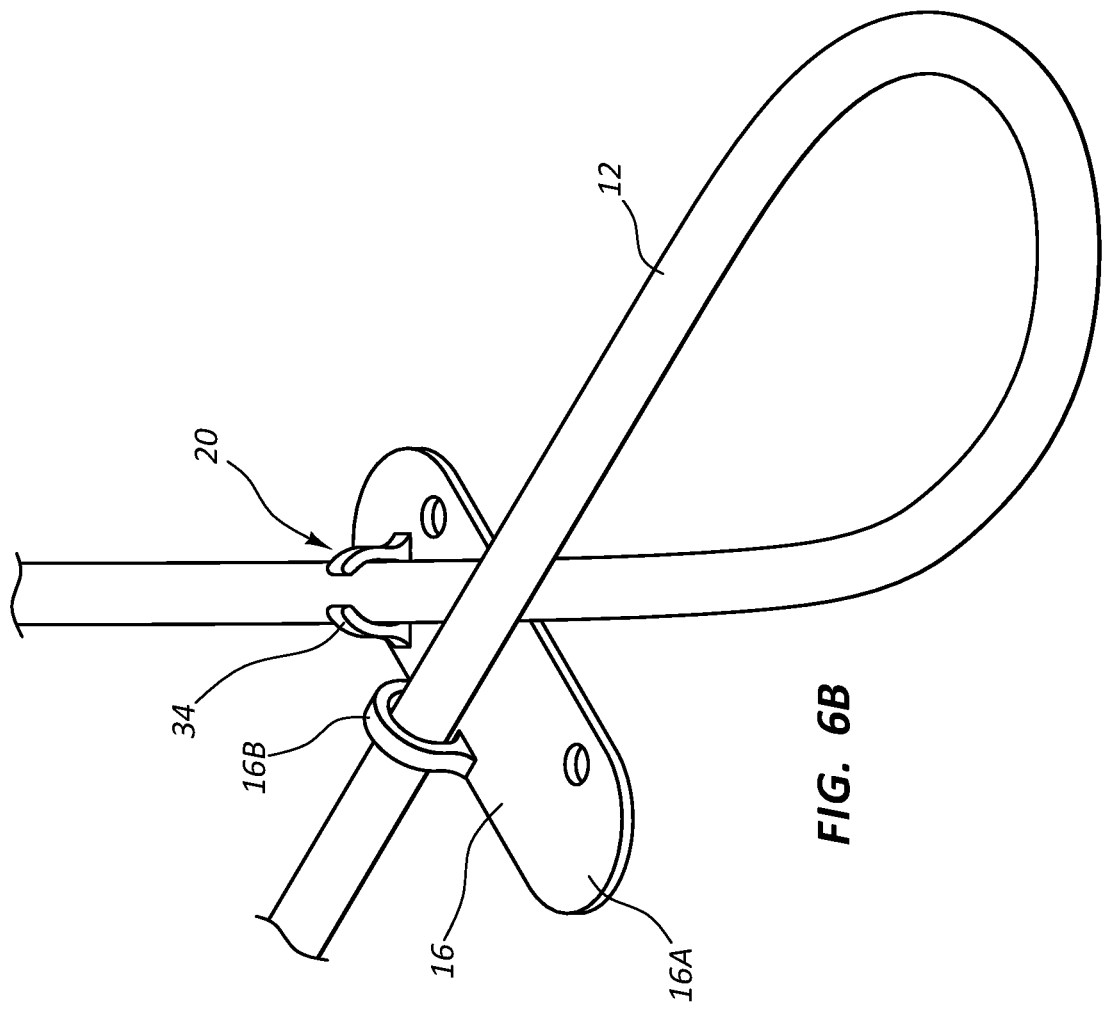
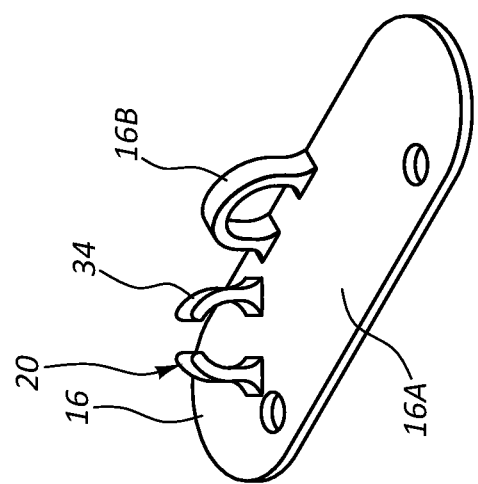
FIG. 6B
FIG. 6A

CURVED CATHETER AND METHODS FOR MAKING SAME

CROSS-REFERENCE TO RELATED APPLICATIONS

This application is a division of U.S. patent application Ser. No. 14/152,599, filed Jan. 10, 2014, now U.S. Pat. No. 10,252,023, which claims the benefit of U.S. Provisional Patent Application No. 61/751,682, filed Jan. 11, 2013, and titled "Systems and Methods for Forming A Pre-Curved Catheter," each of which is incorporated herein by reference in its entirety.

BRIEF SUMMARY

Briefly summarized, embodiments of the present invention are directed to a pre-curved catheter tube of a catheter assembly or other elongate medical device and methods for forming such a device using a heating procedure. Pre-curving of the catheter tube is desirable to impart to the catheter assembly a desired positional configuration when the catheter assembly is inserted into a patient. The heating procedure may include heat sterilization procedures commonly used to sterilize medical devices prior to use.

In one embodiment, a catheter assembly is disclosed, comprising an elongate catheter tube defining at least one lumen, and a tube constraint. The tube constraint is included with the catheter assembly and is configured to temporarily constrain the catheter tube in a curved configuration during a heating procedure of the catheter assembly so as to permanently form the catheter tube in the curved configuration after the heating procedure is complete and the catheter tube is released from the tube constraint.

Examples of catheter assemblies that can benefit from the present disclosure include CVC, PICC, dialysis, peripheral IV and other catheters, though the principles to be described herein can be applied to catheters and elongate medical devices of a variety of configurations.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 3A and 3B show the bifurcation portion of FIG. 2 in multiple configurations;

FIGS. 6A-6D show suture wings including tube constraints according to possible embodiments;

DETAILED DESCRIPTION OF SELECTED EMBODIMENTS

Figure 1A:
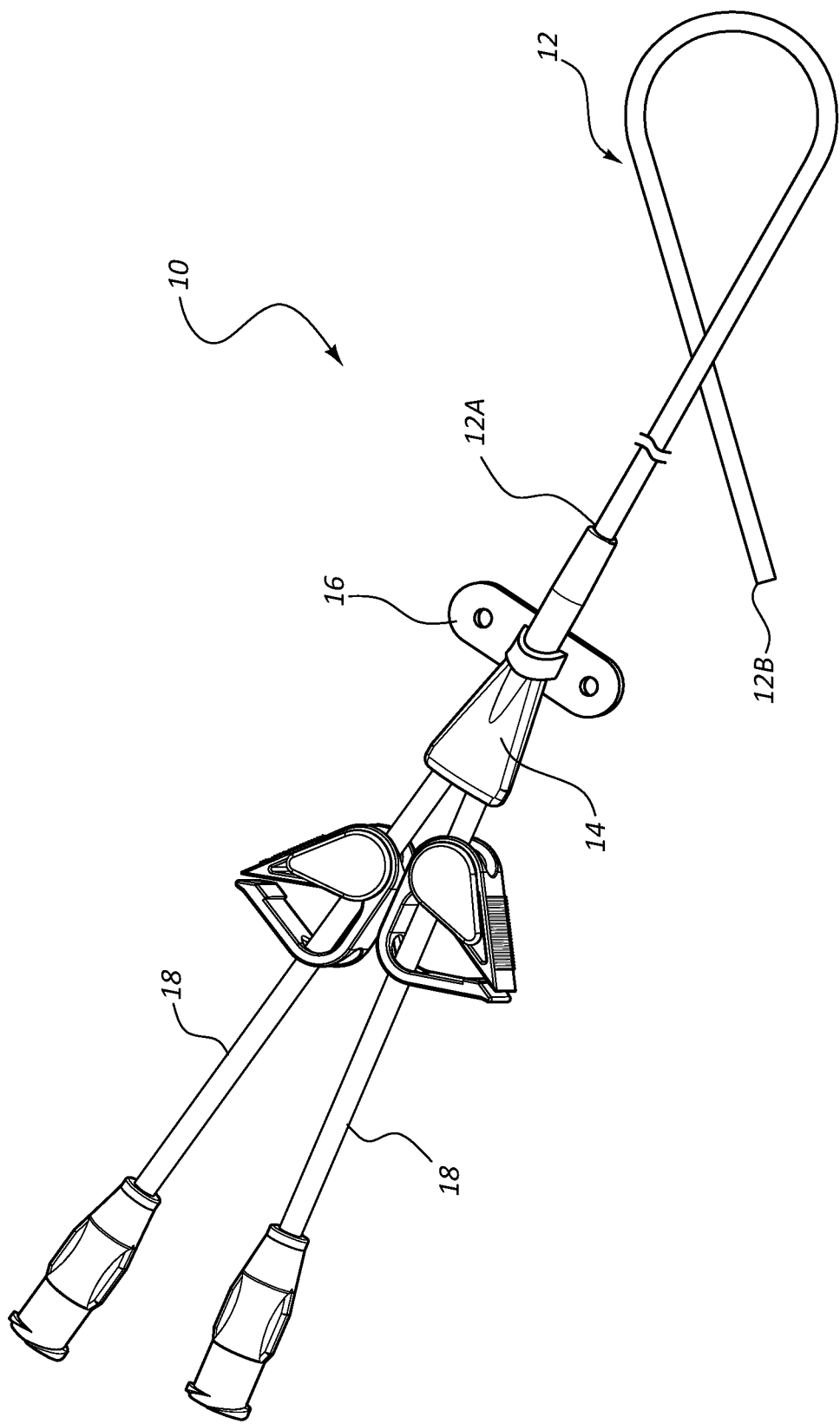
FIGS. 1A and 1B are various views of a catheter assembly including a curved catheter tube according to one embodiment.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to the formation of a pre-curved catheter tube or other elongate medical device using the heat produced in heat sterilization procedures commonly used to sterilize medical devices prior to use. Pre-curving of the catheter tube is desirable to impart to the catheter assembly a desired positional configuration when the catheter assembly is inserted into a patient. Examples of catheter assemblies include CVC, PICC, dialysis, peripheral IV and other catheters, though the principles to be described herein can be applied to catheters and elongate medical devices of a variety of configurations.

Reference is first made to FIG. 1, which shows a catheter assembly ("catheter") 10 configured in accordance with one embodiment. As shown, the catheter assembly ("catheter") 10 includes an elongate catheter tube 12 that defines one or more lumens longitudinally extending between a proximal end 12A and a distal end 12B of the tube. A bifurcation 14 mates with the catheter tube 12 at the proximal end 12A thereof to provide fluid communication between the catheter tube and one or more extension legs 18.

A suture wing 16 is included with the bifurcation 14 for enabling suturing of the catheter assembly 10 to the patient's skin or other location. Though shown here as a discrete portion of the bifurcation, the suture wing in other embodiments can be integrally formed with the bifurcation.

Figure 1B:
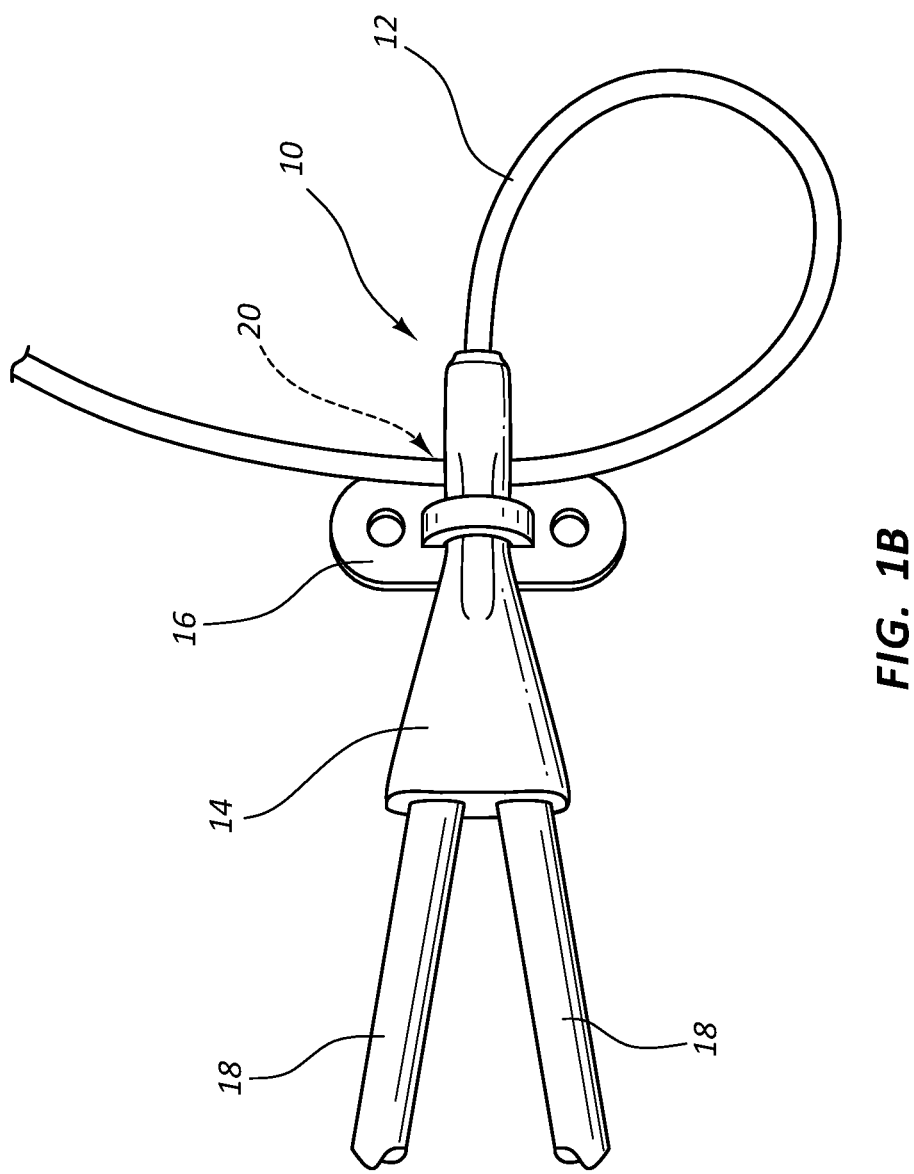

FIGS. 1A and 1B show that the catheter tube 12 is compliant and is disposed in a pre-curved configuration, wherein the tube crosses over itself or over another part of the catheter assembly. This is also referred to herein as an "alphacurve" configuration. In addition to an alphacurve or looped configuration, the catheter tube 12 can be bent or curved in a variety of other configurations. Note also, that, though shown and described herein in connection with medical applications for providing vascular access to a patient, the catheter assembly can be configured differently from what is shown and described herein for a variety of applications. For example, the principles to be taught herein can be applied to a variety of catheter types and configurations, including CVCs, PICCs, PIVs, drainage, feeding, urinary catheters, etc.

Figure 2:
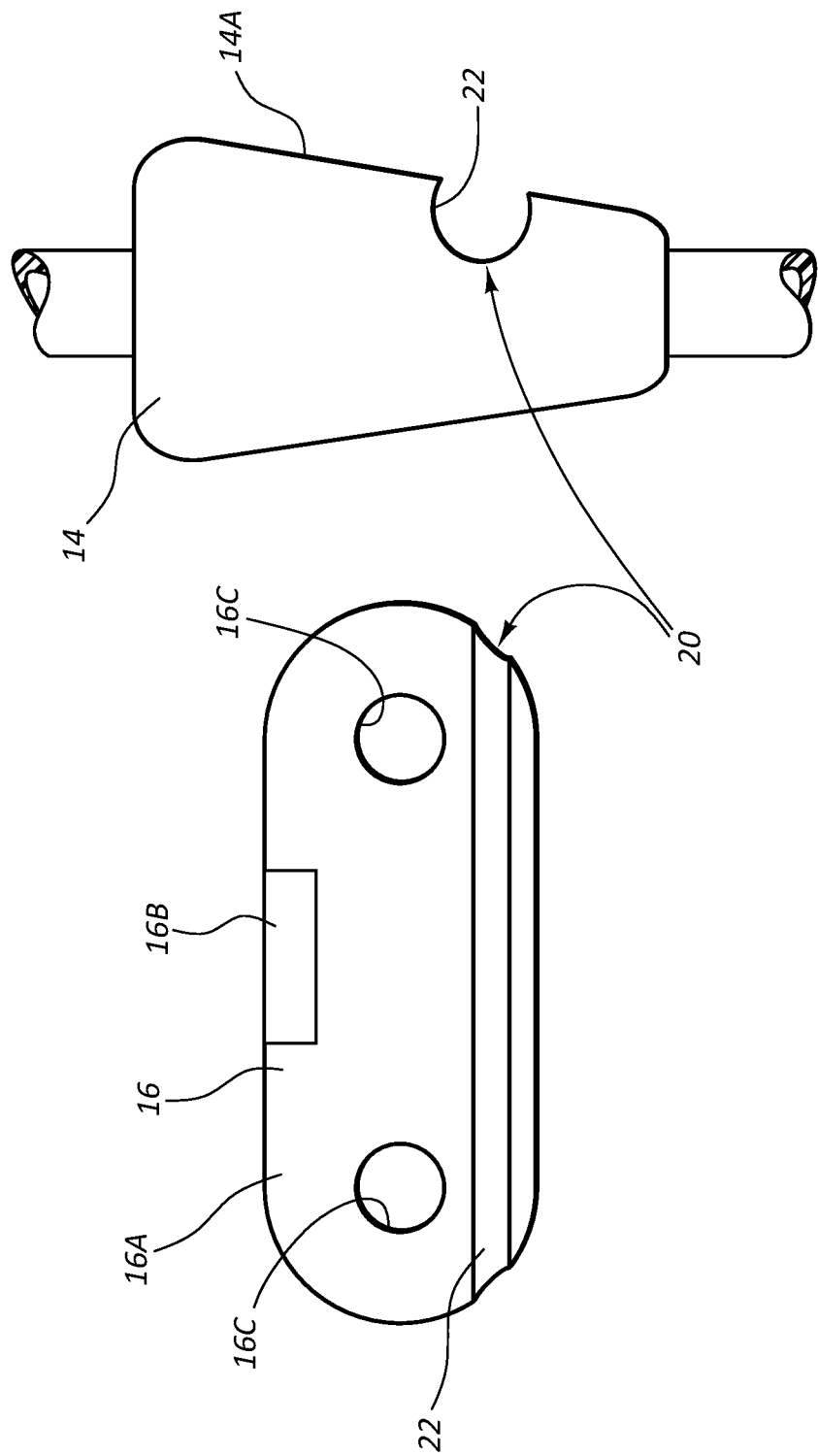
FIG. 2 shows views of a bifurcation portion of the catheter assembly of FIGS. 1A and 1B including a tube constraint according to one embodiment.

As shown in FIG. 1B and additionally illustrated in FIG. 2, the catheter further includes in the present embodiment a tube constraint 20 sized and configured to temporarily constrain the catheter tube 12 in a curved configuration (also referred to herein as a pre-curved configuration), such as that shown in FIG. 1B. Temporary maintenance of the catheter tube 12 in such a curved configuration enables the curve to be permanently set in the catheter tube—via subjecting the constrained catheter tube to a suitable heating procedure—even after the catheter tube is released from the tube constraint, thus desirably producing a pre-curved catheter, similar to that shown in FIG. 1A, which can be used for various medical applications.

The tube constraint 20 of FIG. 1B is shown in FIG. 2 to include notches 22 defined on both the bifurcation 14 and the suture wing 16. In an embodiment, and as best seen in FIG. 2, at least the bifurcation portion of the tube constraint may be mated with the catheter tube 12 such that it is permanently included with, or permanently attached to, the catheter assembly 10. In detail and as shown, an elongate, laterally extending notch 22A is defined in a base 16A of the suture wing while a corresponding notch 22B is defined on a bottom surface 14A of the bifurcation. When the suture wing 16 is rotatably attached to the bifurcation 14 via receipt of a distal portion of the bifurcation through a loop 16B of the suture wing, the notches 22A, 22B align such that a portion of the looped catheter tube 12 can be interposed between the notches in a sandwiched configuration in such a way as to securely hold yet not substantially compress the tube. This positional relationship maintains the catheter tube 12 in the looped configuration shown in FIG. 1B until the tube is removed from the notches 22A and 22B, as discussed below. As such, the notches 22A and 22B are suitably sized to perform the above functionality. In one embodiment, therefore, the notches can be sized according to the diameter size of the catheter tube, which size can vary as appreciated by one skilled in the art. In another embodiment, the notches are sized so as to provide more or less compression of the catheter tube, as may be desired. Note further that the suture wing 16 further includes a pair of holes 16C for enabling the passage of sutures therethrough in securing the catheter 10 to the patient's skin.

FIGS. 3A and 3B show that the notches 22A, 22B can be adjusted in position along the bodies of the suture wing 16 and the bifurcation 14 so as to provide different degrees of catheter tube bend. For instance, FIG. 3A shows the notches 22A and 22B disposed relatively more distally with respect to the structure of the catheter 10 so as to provide a relatively smaller radius of curvature for the looped catheter tube 12 when it is received within the notches. This in turn produces a relatively more tightly-looped curve in the catheter tube 12 after formation. In contrast, FIG. 3B shows the notches 22A and 22B disposed relatively more proximally with respect to the structure of the catheter 10 so as to provide a relatively larger radius of curvature for the looped catheter tube 12 when it is received within the notches. This in turn produces a relatively less tightly-looped curve in the catheter tube 12 after formation. Note that other locations on the catheter assembly 10 can be employed for fixing the catheter tube 12 in a looped configuration.

The looped or curved configuration of the catheter tube 12 discussed above is initially maintained by the tube constraint 20, e.g., the notches 22A, 22B, such as is seen in FIG. 1B. The constrained catheter tube 12 is then subjected to a heating procedure of sufficient time, temperature, and duration as to permanently set the curved configuration of the tube so as to resemble that shown in FIG. 1A, as desired.

In the present embodiment, a heat sterilization procedure to sanitize the catheter assembly before shipment to and use by customers occurs after catheter manufacture and further serves as the heating procedure to permanently set the curved configuration of the catheter tube 12 (FIG. 1A). Though other types of heat-based sterilizing procedures may be used, in the present embodiment an ethylene oxide ("ETO") sterilization procedure is employed to sterilize the catheter 10. The heat produced during the ETO sterilization procedure is sufficient in the present embodiment to permanently set the catheter tube 12 in the curved configuration shown in FIG. 1A even after the tube is released from the tubing constraint 20 after the ETO sterilization procedures is complete. As mentioned, other heat-based sterilization or non-sterilizing heating procedures can be employed to impart to the catheter tube the curved configuration. Examples include steam sterilization, autoclaving, etc.

In the present embodiment, the catheter tube 12 and bifurcation 14 include an aliphatic polyether polyurethane sold under the name TECOFLEX®, by Lubrizol Advanced Materials, Inc. of Cleveland, Ohio, though other thermoplastics can also be acceptably employed from which the catheter tube is manufactured so as to impart a permanent curve to the catheter tube under heat sterilization or other suitable heating procedure. In one embodiment, a thermoplastic falling within a hardness range of between about 65 D and about 95 A can be used, though thermoplastics outside of this range can also be employed.

In light of the above and in connection with the presently discussed figures, in one embodiment the curved configuration can be permanently set in the catheter tube 12 by first manufacturing the catheter assembly 10 to include the components shown and described in connection with FIG. 1A, or more or fewer components as may be appreciated by one skilled in the art. The catheter tube 12 can then be placed in a curved (e.g., looped) configuration by placing a portion thereof into the tube constraint 20, e.g., the notches 22A, 22B (FIGS. 1B, 2) in the present embodiment, or other suitable tube constraint such that the curved configuration is temporarily maintained. The catheter assembly is then optionally packaged in a package or suitable container, and subsequently placed in a chamber where it is subjected to ETO or other suitable form of heat sterilization for a predetermined amount of time and temperature. This process permanently sets the curved configuration in the catheter tube 12. As mentioned, other suitable heating procedures can be used in place of ETO or other heat-based sterilization procedures. Though the catheter tube 12 can then be removed from the notches 22A, 22B that form the tube constraint 20 if desired, in another embodiment the catheter tube is left in the notches or other suitable tube constraint within the sealed and sterilized container until the catheter assembly 10 is removed by the clinician in preparation for insertion into the patient. Variations to this process are possible, as appreciated by one skilled in the art. Note that after the curve is permanently set and the catheter tube is removed from the tube constraint, a limited amount of relaxation of the catheter tube curve may occur. For instance, in one embodiment the catheter tube 12 as shown constrained in FIG. 1B may, after having its curve permanently set and being released from the tube constraint, relax to the shape shown in FIG. 1A.

In various prophetic examples, permanent curving of polyurethane CVC and PICC catheter tubes (including a bifurcation including a suture wing of low-density polyethylene ("LDPE") or thermoplastic elastomer) via use of a tube constraint during ETO heat sterilization procedures are believed achievable at the following temperatures and time combinations: about 55 degrees Celsius ("C") for about 15 minutes; about 55 degrees C. for about one hour; about 55 degrees C. for about 12 hours; about 100 degrees C. for about 12 hrs; about 100 degrees C. for about one hour; about 100 degrees C. for about 15 minutes; about from about 220 to about 255 degrees Fahrenheit ("F") for about 65 to about 80 seconds; and from about 230 to about 240 degrees F. for about 270 to about 330 seconds. Note that the above examples, like typical ETO sterilization procedures, are performed under vacuum, though it is believed that the presence of a vacuum does not substantially affect the ability of the heating procedure to set the catheter tube in a permanent curved configuration. Generally, it is understood that permanent forming of the catheter tube in accordance with the present disclosure depends on several factors, including tube material, tube thickness, lumen geometry, etc. It is further appreciated that a wide variety of time and temperature combinations for the heating procedure are possible. Generally, relatively lower heating procedure temperatures will require relatively more time with the catheter tube constrained in its curved configuration during heating in order for the curve to be permanently set in the tube. Correspondingly, relatively higher heating procedure temperatures require relatively less time of constraint to set the curve during heating.

Figure 4B:
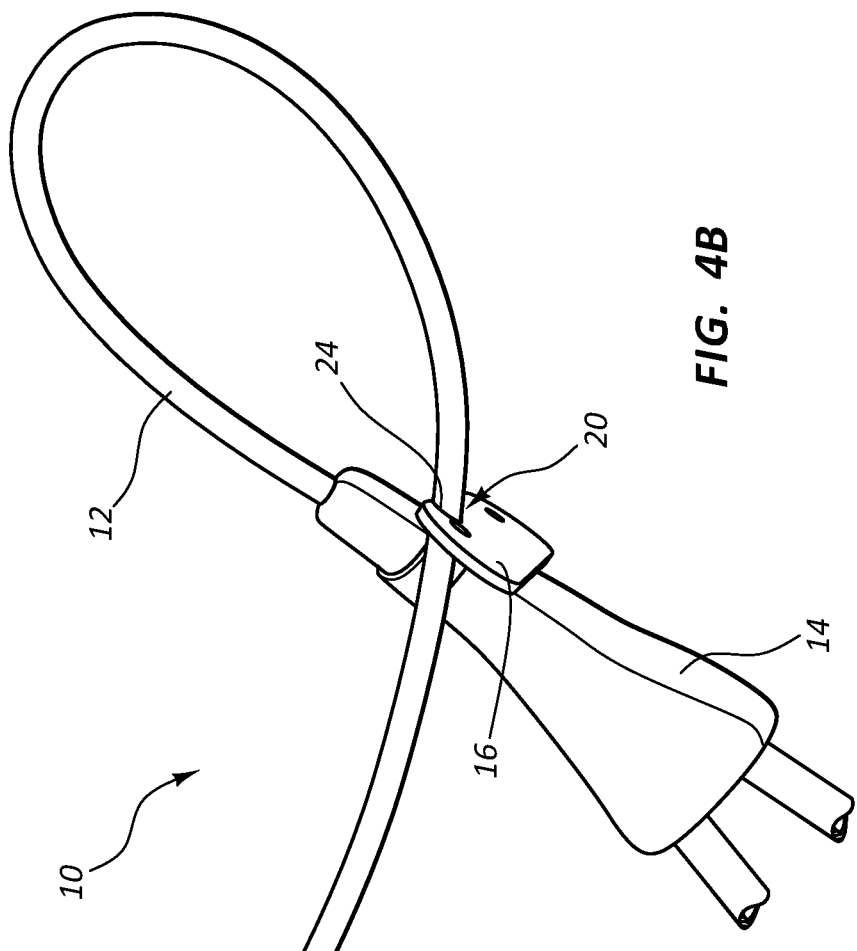
FIGS. 4A and 4B show various views of a bifurcation portion of a catheter assembly including a tube constraint according to one embodiment.
Figure 4A:
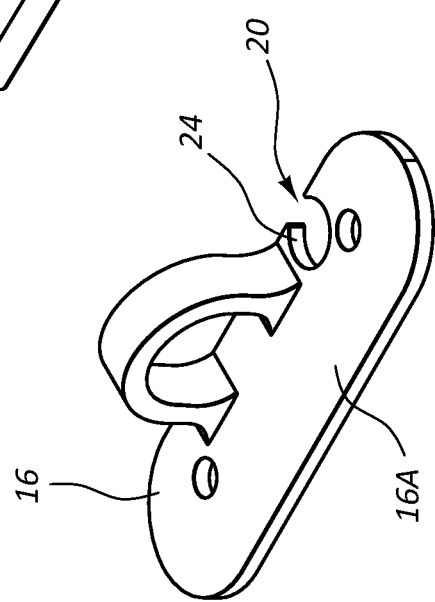

FIGS. 4A and 4B depict the tube constraint 20 according to another embodiment, wherein the tube constraint includes a notch 24 defined through the base 16A of the bifurcation suture wing 16. The notch 24 is sized so that a portion of the catheter tube 12 is retained thereby without constricting the tube portion. The notch 24 can be configured to have a break or open portion in its perimeter such that the catheter tube 12 can be pushed through the open portion into the notch. In another embodiment, the notch perimeter is completely closed off such that the distal end 12B of the catheter tube 12 must be first passed through the notch for the notch to receive the tube. Note that in the present embodiment the suture wing 16 is configured to swivel about the body of the bifurcation 14 such that the orientation of the curved portion of the catheter tube 12 can be adjusted according to the desired tube orientation once the curve is permanently set via the ETO heat sterilization or other suitable heating procedure.

Figure 5A:
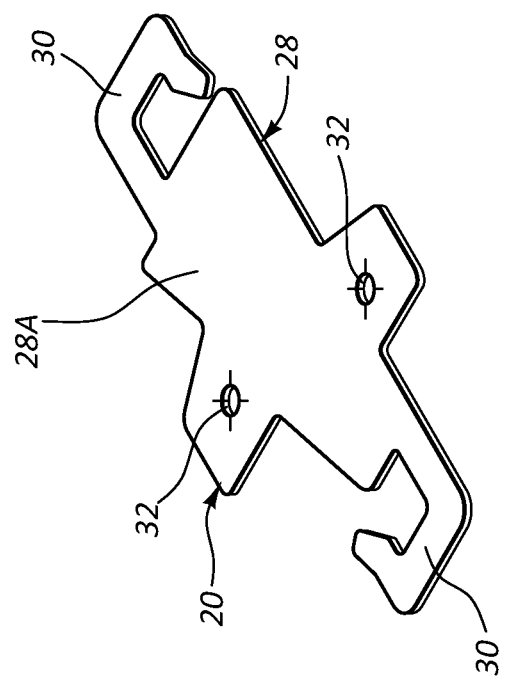
FIGS. 5A and 5B show various views of a catheter assembly including a tube constraint according to one embodiment.
Figure 5B:
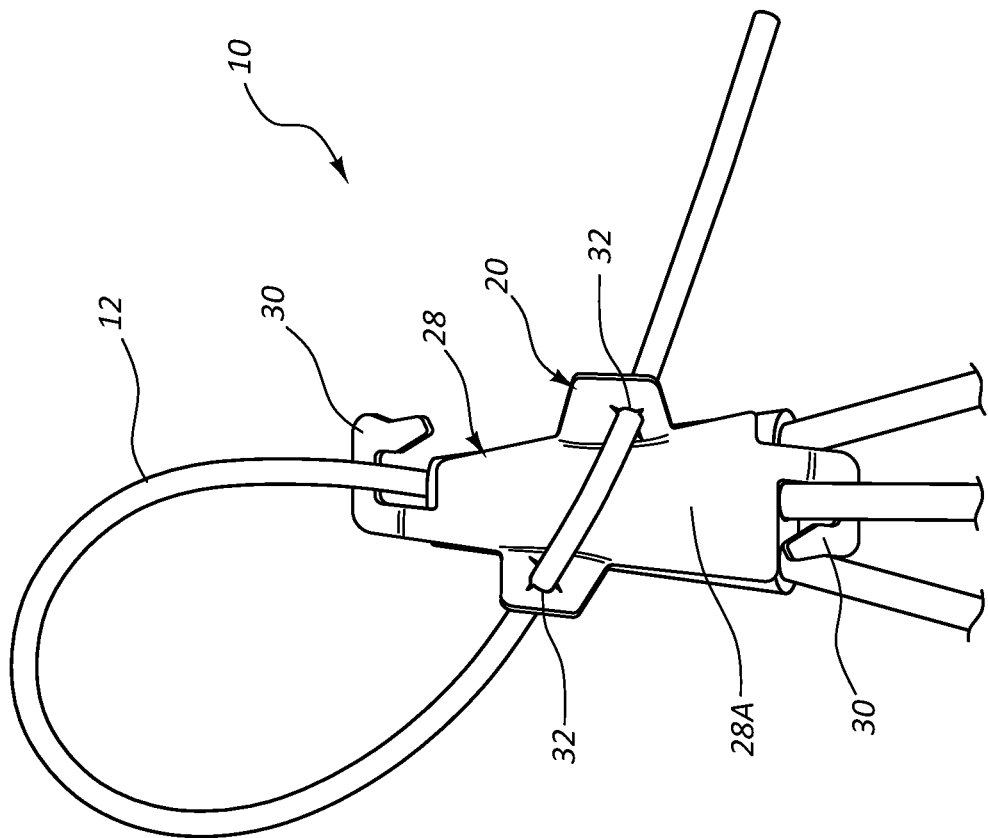

FIG. 5 shows the tube constraint 20 according to yet another embodiment, wherein the tube constraint includes a form 28 that is shaped and configured to constrain a portion of the catheter tube 12 in a curved configuration in preparation for permanent forming of the curve via ETO sterilization or other suitable heating procedure. As shown, the form 28 includes a relatively flat, compliant body 28A including a suitably strong material, such as paper, fiberboard, cardstock, cardboard, etc. In one embodiment, the form 28 includes a durable spun-bonded olefin sheet sold under the trademark TYVEK® by E. I. du Pont de Nemours and Co., though various other suitable materials can also be employed.

The form body 28A defines two hooked segments 30 that engage portions of the catheter assembly 10: one to wrap about a proximal portion of the catheter tube 12; the other to wrap about one of the extension legs 18. The form body 28A further defines two holes 32 through which a portion of the curved catheter tube passes. The holes 32 are sized so as to suitable restrain the catheter tube 12, thus enabling the form 28 to temporarily maintain the tube in a desired curved configuration. Once the catheter tube 12 has been subjected to a suitable heating procedure to permanently set the curve thereof, the form 28 can be removed from the catheter assembly 10 as desired. In one embodiment, instructions are printed on the form 28 or otherwise provided to assist the user in removing and/or disposing of the form. In one embodiment, the form 28 can be configured such that it can be ripped/cut apart to remove it from the catheter assembly 10. For instance, form in one embodiment can include perforations to ease removal from the catheter assembly. Note that the particular shape, size, and configuration of the form can vary from what is shown and described herein.

Figure 6C:
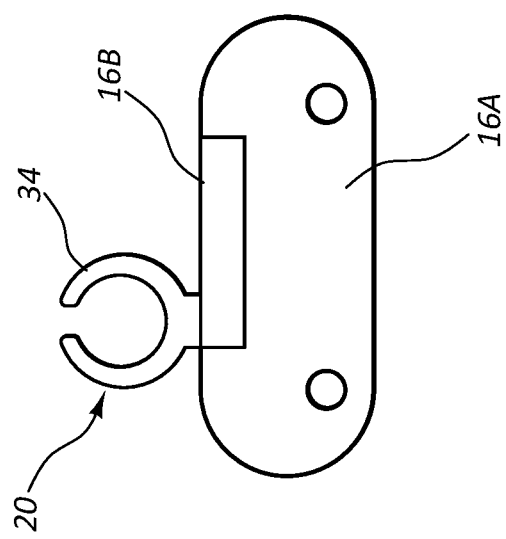
Figure 6D:
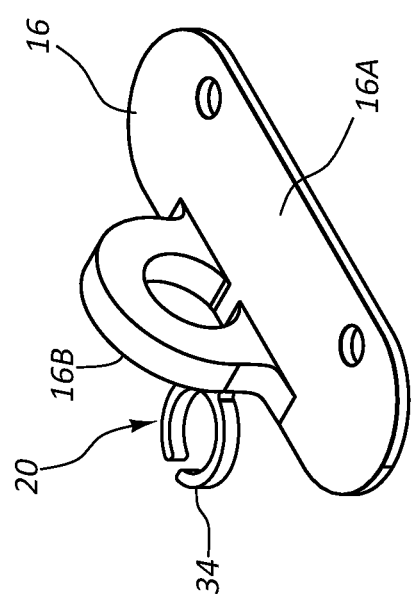

FIGS. 6A-6D depict details of the tube constraint 20 according to yet another embodiment, wherein the tube constraint includes a clip 34 disposed on a portion of the suture wing 16 and sized to temporarily retain therein a portion of the catheter tube 12 in the curved configuration. As illustrated, the clip 34 can be variously positioned on the suture wing 16 or other catheter-related component, such as the main body of the bifurcation and can be removable in one embodiment. In particular, FIG. 6A shows the clip 34 extending from the base 16A of the suture wing 16 in such a way as to constrain the catheter tube 12 as shown in FIG. 6B. In contrast, FIGS. 6C and 6D show the clip extending from a portion of the loop 16B of the suture wing 16. Note that various other positional placements of the clip 34 are possible, both on the suture wing or bifurcation, or elsewhere on the catheter assembly 10.

Figure 7:
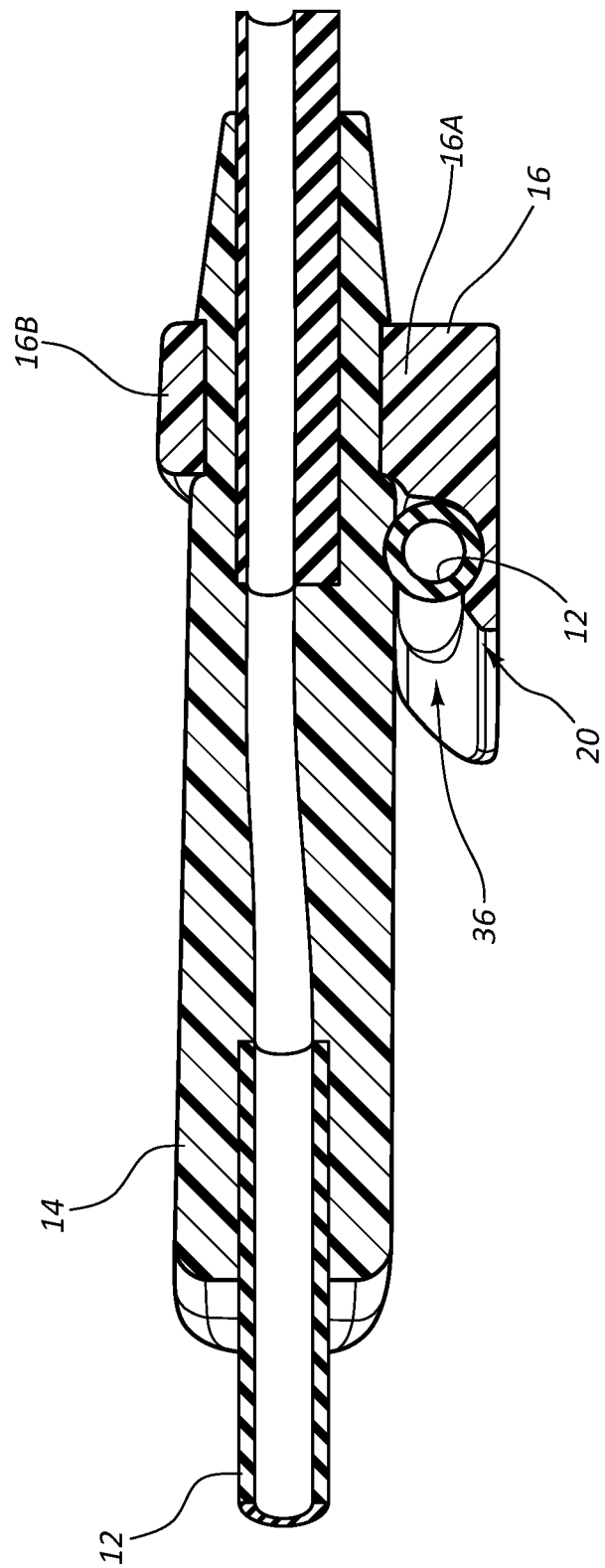
FIG. 7 shows a cross sectional view of a bifurcation portion of a catheter assembly according to one embodiment.

FIG. 7 depicts details of the tube constraint 20 according to yet another embodiment, wherein the tube constraint includes a chamfered pocket 36 that can be included in the design of the base 16A of the suture wing 16. The chamfered pocket 36 is configured so as to facilitate ease of insertion into the pocket of a portion of the catheter tube 12 without negatively affecting the retention force needed to retain the tube therein. The particular angle of the chamfer or other configuration of the pocket 36 can vary from what is shown and described herein.

Figure 8:
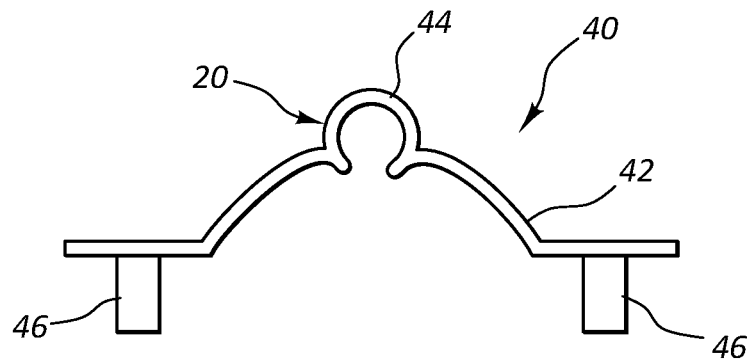
FIG. 8 is a side view of a tube constraint for a catheter assembly according to one embodiment.
Figure 9:
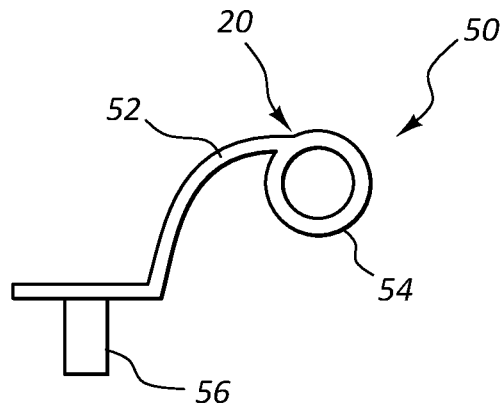
FIG. 9 is a side view of a tube constraint for a catheter assembly according to one embodiment.
Figure 10:
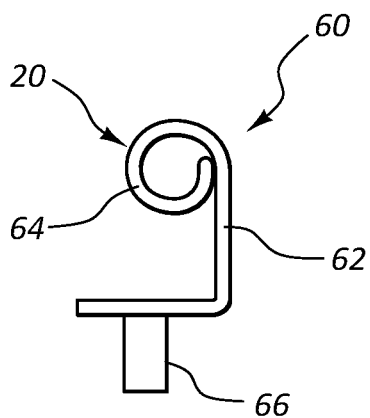
FIG. 10 is a side view of a tube constraint for a catheter assembly according to one embodiment.

FIGS. 8-10 depict details of the tube constraint 20 according to yet other embodiments. In particular, FIG. 8 shows the tube constraint 20 as including an attachment piece 40, which in turn includes a body 42 that defines a clip portion 44 that is configured to receive therein a portion of the catheter tube 12 in order to hold it in a curved configuration. The attachment piece 40 further includes pegs 46 sized and configured to be received within the holes 16C of the suture wing 16 of the catheter assembly 10 (FIGS. 1A, 1B, 2) so as to temporarily secure the attachment piece in place with the catheter assembly. When forming of the catheter tube 12 is complete, the attachment piece 40 can be removed from the catheter assembly and discarded. The pegs 46 are sized to provide a removable interference fit with the suture wing holes 16C, in one embodiment. In other embodiments, other solutions for securing the attachment piece to the catheter assembly can be provided.

FIG. 9 depicts details of the tube constraint 20 according to yet another embodiment, wherein the tube constraint includes an attachment piece 50, which in turn includes a body 52 that defines a hole 54 that is configured to receive therethrough a portion of the catheter tube 12 in order to hold it in a curved configuration. The attachment piece 50 further includes a peg 56 sized and configured to be received within one of the holes 16C of the suture wing 16 of the catheter assembly 10 (FIGS. 1A, 1B, 2) so as to temporarily secure the attachment piece in place with the catheter assembly. When forming of the catheter tube 12 is complete, the attachment piece 50 can be removed from the catheter assembly and discarded. The peg 56 is sized to provide a removable interference fit with the suture wing holes 16C, in one embodiment. In other embodiments, other solutions for securing the attachment piece to the catheter assembly can be provided.

FIG. 10 depicts details of the tube constraint 20 according to yet another embodiment, wherein the tube constraint includes an attachment piece 60, which in turn includes a body 62 that defines a loop portion 64 that is configured to receive therethrough a portion of the catheter tube 12 in order to hold it in a curved configuration. The attachment piece 60 further includes a peg 66 sized and configured to be received within one of the holes 16C of the suture wing 16 of the catheter assembly 10 (FIGS. 1A, 1B, 2) so as to temporarily secure the attachment piece in place with the catheter assembly. When forming of the catheter tube 12 is complete, the attachment piece 60 can be removed from the catheter assembly and discarded. The peg 66 is sized to provide a removable interference fit with the suture wing holes 16C, in one embodiment. In other embodiments, other solutions for securing the attachment piece to the catheter assembly can be provided. Note that, in the embodiments of FIGS. 8-10, other solutions for attaching to the catheter tube, apart from holes, clips, and loops, could be used and that these components can be interchanged between the designs shown in FIGS. 8-10. In yet another embodiment, a dual-clip device can be employed, wherein a first clip attaches to a first portion of the catheter tube and a second clip attaches to a second portion of the catheter tube to maintain the catheter tube in a curved, e.g., a looped, configuration.

In addition the above embodiments, other tubing constraint configurations for retaining the catheter tube in a pre-curved configuration can be employed, including a portion of adhesive including a glue dot or adhesive tape, a feature included with the catheter assembly container, a silicone insert, a removable clip, etc. In one embodiment the tube constraint 20 prevents the catheter tube 12 from coming into contact with another portion of the tube or other like-material components, such as the body of the bifurcation 14, so as to avoid knitting of the two components together during heat-based sterilization. Also, the tubing constraint is configured in one embodiment to hold the catheter tube without damaging or deforming it.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method for curving a catheter tube of a catheter assembly, the catheter assembly including a tube constraint formed by features of both a bifurcation hub and a suture wing of the catheter assembly, the method comprising:
    constraining the catheter tube into a curved configuration using the tube constraint;
    heating the catheter tube in the curved configuration for a predetermined time at a predetermined temperature; and
    releasing the catheter tube from the tube constraint after the heating is complete, wherein the catheter tube permanently retains the curved configuration.

2. The method according to claim 1, wherein the heating step includes utilizing a heat sterilization procedure.

3. The method according to claim 2, wherein the heating sterilization procedure includes utilizing an ethylene oxide sterilization procedure.

4. The method according to claim 3, wherein the ethylene oxide sterilization procedure is performed at a temperature of at least about 55 degrees Celsius.

5. The method according to claim 4, wherein the ethylene oxide sterilization procedure is performed for a time of at least about 15 minutes.

6. The method according to claim 1, wherein the constraining step comprises forming a catheter tube loop in the curved configuration.

7. The method according to claim 1, wherein the tube constraint includes a first notch in the suture wing and a second notch in the bifurcation hub, and wherein the constraining step comprises inserting the catheter tube in the first notch and the second notch.

8. The method according to claim 7, wherein the first notch and the second notch are aligned, and wherein the constraining step comprises inserting the catheter tube between the suture wing and the bifurcation hub.

9. A method for curving a catheter tube of a catheter assembly, the catheter assembly comprising a bifurcation hub including a tube constraint, the method comprising:
    constraining the catheter tube into a curved configuration by coupling the catheter tube to the bifurcation hub;
    heating the catheter tube in the curved configuration for a predetermined time at a predetermined temperature; and
    releasing the catheter tube from the tube constraint after the heating is complete, wherein the catheter tube permanently retains the curved configuration.

10. A method for curving a catheter tube of a catheter assembly, the catheter assembly including a tube constraint comprising a suture wing, the suture wing including a notch designed to constrain the catheter tube, the method comprising:
    constraining the catheter tube into a curved configuration by inserting the catheter tube into the notch of the suture wing;
    heating the catheter tube in the curved configuration for a predetermined time at a predetermined temperature; and
    releasing the catheter tube from the tube constraint after the heating is complete, wherein the catheter tube permanently retains the curved configuration.

11. A method for curving a catheter tube of a catheter assembly, the catheter assembly including a tube constraint comprising a suture wing including a clip designed to constrain the catheter tube, the method comprising:
    constraining the catheter tube into a curved configuration by inserting the catheter tube into the clip of the suture wing;
    heating the catheter tube in the curved configuration for a predetermined time at a predetermined temperature; and
    releasing the catheter tube from the tube constraint after the heating is complete, wherein the catheter tube permanently retains the curved configuration.

12. A method for curving a catheter tube of a catheter assembly, the catheter assembly including a tube constraint comprising a spun-bonded olefin sheet including one or more openings designed to receive the catheter tube, the method comprising:
   constraining the catheter tube into a curved configuration by inserting the catheter tube into the one or more openings of the sheet;
   heating the catheter tube in the curved configuration for a predetermined time at a predetermined temperature; and
   releasing the catheter tube from the tube constraint after the heating is complete, wherein the catheter tube permanently retains the curved configuration.

13. A method for curving a catheter tube of a catheter assembly, the catheter assembly including a tube constraint, the method comprising:
   constraining the catheter tube into a curved configuration by inserting a portion of the catheter tube in at least one notch provided on the catheter assembly;
   heating the catheter tube in the curved configuration for a predetermined time at a predetermined temperature; and
   releasing the catheter tube from the tube constraint after the heating is complete, wherein the catheter tube permanently retains the curved configuration.

* * * * *